US006764694B1

(12) United States Patent
Spireas

(10) Patent No.: US 6,764,694 B1
(45) Date of Patent: *Jul. 20, 2004

(54) STABLE FORMULATIONS OF ACE INHIBITORS, AND METHODS FOR PREPARATION THEREOF

(75) Inventor: Spiridon Spireas, Newton, PA (US)

(73) Assignee: Mutual Pharmaceutical Co., Inc., Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/492,584

(22) Filed: Jan. 27, 2000

Related U.S. Application Data

(63) Continuation-in-part of application No. 09/387,419, filed on Aug. 31, 1999.

(51) Int. Cl.[7] .............................................. A61K 9/20
(52) U.S. Cl. ...................... 424/464; 424/501; 424/465; 424/464; 424/440; 424/489
(58) Field of Search ................... 424/501, 464, 424/465, 440, 489

(56) References Cited

U.S. PATENT DOCUMENTS

| | | | | |
|---|---|---|---|---|
| 4,743,450 A | * | 5/1988 | Harris et al. ................. | 424/440 |
| 5,350,582 A | * | 9/1994 | Merslavic et al. ........... | 424/464 |
| 5,350,584 A | * | 9/1994 | McClelland et al. ......... | 424/501 |
| 5,562,921 A | * | 10/1996 | Sherman ...................... | 424/465 |
| 5,573,780 A | * | 11/1996 | Sherman ...................... | 424/464 |
| 5,637,730 A | * | 6/1997 | Murthy et al. ............... | 548/540 |
| 5,690,962 A | * | 11/1997 | Sherman ...................... | 424/489 |
| 6,153,223 A | * | 11/2000 | Apelian et al. .............. | 424/489 |
| 6,555,551 B1 | * | 4/2003 | Spireas ........................ | 514/299 |
| 2003/0225124 A1 | * | 12/2003 | Spireas ........................ | 514/310 |

FOREIGN PATENT DOCUMENTS

| | | | |
|---|---|---|---|
| CA | 2028665 | * | 4/1991 |
| EP | 0 425 892 A2 | | 10/1990 |
| WO | PCT/US00/23539 | | 12/2000 |

OTHER PUBLICATIONS

Hawley's Condensed Chemical Dictionary, Thirteenth Edition, p. 229.*
Liberman et al. (eds.), *Theory & Practice of Industrial Pharmacy*, 3rd Edition, Philadelphia, PA, 1986.
*Remington's Pharmaceutical Sciences*, 18th Edition, Easton, PA, Mack Publishing Co., 1990.

* cited by examiner

Primary Examiner—Sabiha Qazi
(74) Attorney, Agent, or Firm—Woodcock Washburn LLP

(57) ABSTRACT

The present invention provides stable formulations of ACE inhibitors, especially enalapril maleate, that can be manufactured in a time efficient, cost effective manner. Such formulations can be prepared simply and on a large industrial scale. The present invention also provides methods for the preparation of stable formulations of ACE inhibitors, especially enalapril maleate.

22 Claims, 2 Drawing Sheets

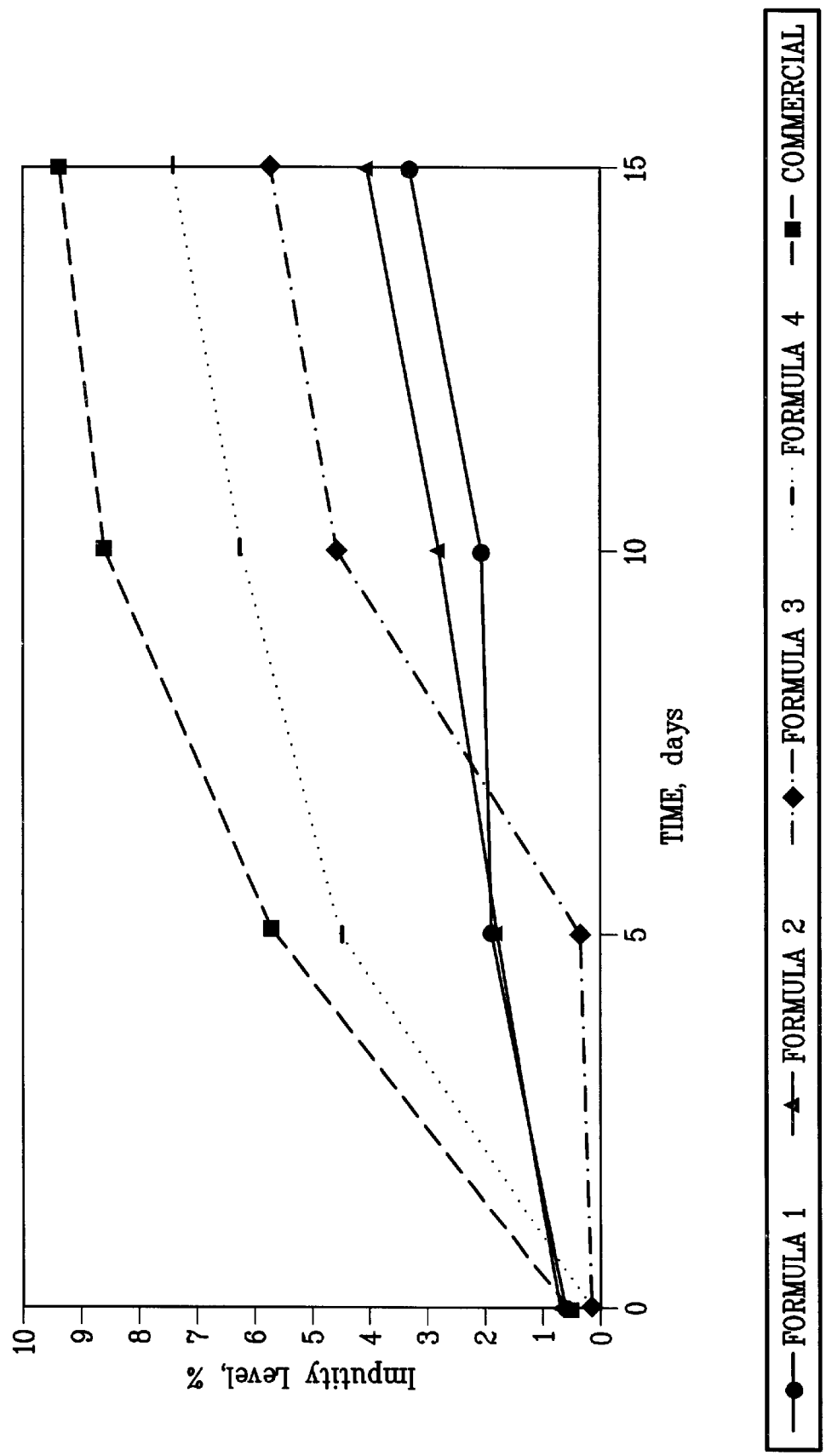

ofmethods:title">STABLE FORMULATIONS OF ACE INHIBITORS, AND METHODS FOR PREPARATION THEREOF This Application is a continuation-in-part of U.S. Application Ser. No. 09/387,419 filed Aug. 31, 1999.

FIELD OF THE INVENTION

The present invention relates to stable formulations of ACE inhibitors and similar drugs, especially enalapril maleate. The present invention also relates to methods for the preparation of stable formulations of ACE inhibitors.

BACKGROUND OF THE INVENTION

ACE inhibitors, or inhibitors of Angiotensin Converting enzymes, are drugs useful in the treatment of cardiovascular disorders, especially hypertension. However, it has been widely observed that ACE inhibitors are susceptible to breakdown, especially due to degradation and/or cyclization between the time of manufacture and the time of desired usage. Breakdown of ACE inhibitors has been found to occur both in solid and in liquid states. As breakdown of ACE inhibitor increases, the concentration of available, functional ACE inhibitor decreases. Also, at least some of the degradation products of such breakdown are believed to be deleterious. Accordingly, such breakdown is to be avoided.

ACE inhibitors include, but are not limited to, enalapril maleate and similar salts; quinapril hydrochloride and similar salts; benazepril hydrochloride and similar salts; moexipril hydrochloride and similar salts; lisonopril hydrochloride and similar salts; and indopril hydrochloride and similar salts. Typical breakdown products of ACE inhibitors include, but are not limited to, enalaprilat and/or enalapril-diketopiperazine (DKP) for enalapril species, quinalaprilat and/or quinapril-DKP for quinapril drugs, and other breakdown products well-known to those of skill in the art.

Methods for the formulation of ACE inhibitors into stable solid dosage forms have been previously described. For example, Merslavic et al., in U.S. Pat. No. 5,350,582, describe the formulation of enalapril sodium through the suspension of enalapril maleate in water with certain metal compounds. Full conversion to enalapril sodium is said to be indicated by a final "clear" solution. However, the suspension of enalapril maleate in water is extremely time-consuming due to the low wetability of enalapril maleate. Consequently, the residence time of the drug in the water is high. A high residence time is believed to facilitate significant hydrolysis of the product and lead to a drop in drug purity. Further, following the procedures described by Merslavic et al., high unit dose weights of lactose and starch are required.

Sherman et al., in U.S. Pat. Nos. 5,690,962 and 5,573,780, have described methods for the formulation of enalapril sodium. Instead of dispersing enalapril maleate in water, Sherman et al. describe "dry-blending" the enalapril maleate with an alkaline sodium powder and another powder excipient such as lactose. This "blend" is then granulated with water to initiate the acid-base conversion of enalapril maleate to enalapril sodium. Unlike the process described by Merslavic et al., Sherman provides no easily determinable endpoint of complete conversion of enalapril maleate to enalapril sodium Therefore, it is likely that significant batch-to-batch variations in purity of the product, i.e., amount of enalapril sodium, will exist in large scale production scenarios. Additionally, the Sherman et al. process may involve a time-consuming conversion of enalapril maleate to enalapril sodium, such that the product is vulnerable to breakdown and a drop in drug purity.

Sherman et al., in U.S. Pat. No. 5,562,921, also describe the manufacture of enalapril sodium formulations with improved resistance to decomposition. These formulations are said to be more resistant to decomposition due to restrictions in the excipients used in the process. However, the excipients set forth by Sherman as offering improved resistance to decomposition lead to formulations which lack sufficient hardness, an important quality in pharmaceutical formulations.

Harris et al., in U.S. Pat. No. 4,743,450, describe the use of stabilizers to minimize the cyclization, hydrolysis, and coloration of ACE inhibitors.

There remains a long-standing need for stable formulations and methods of preparation of ACE inhibitors. There is a further need for formulations and methods of preparation of ACE inhibitors that minimize breakdown of the product, that are inexpensive and time-efficient, and that have improved uniformity from batch to batch. Additionally, there is a need for methods of preparation and formulations of ACE inhibitors which are greatly reduced in breakdown products during preparation and/or subsequent storage.

SUMMARY OF THE INVENTION

The present invention relates to stable formulations of ACE inhibitors, especially enalapril sodium and similar drugs. The present invention also relates to time-efficient methods of preparing stable formulations thereof. Further, the present invention provides formulations and methods of preparation of ACE inhibitors that minimize breakdown of the products during preparation and/or subsequent storage thereof. The present invention also relates to products of the methods of preparing stable formulations of ACE inhibitors. The present invention also provides formulations of ACE inhibitors substantially free of harmful and/or undesired breakdown products. It is now possible to prepare such formulations which are substantially free of these contaminants. These and other embodiments of the present invention will readily occur to those of ordinary skill in the art in view of the disclosure herein.

BRIEF DESCRIPTION OF THE DRAWINGS

FIG. 2 depicts impurity levels in different formulations of enalapril sodium.

Figure 1:
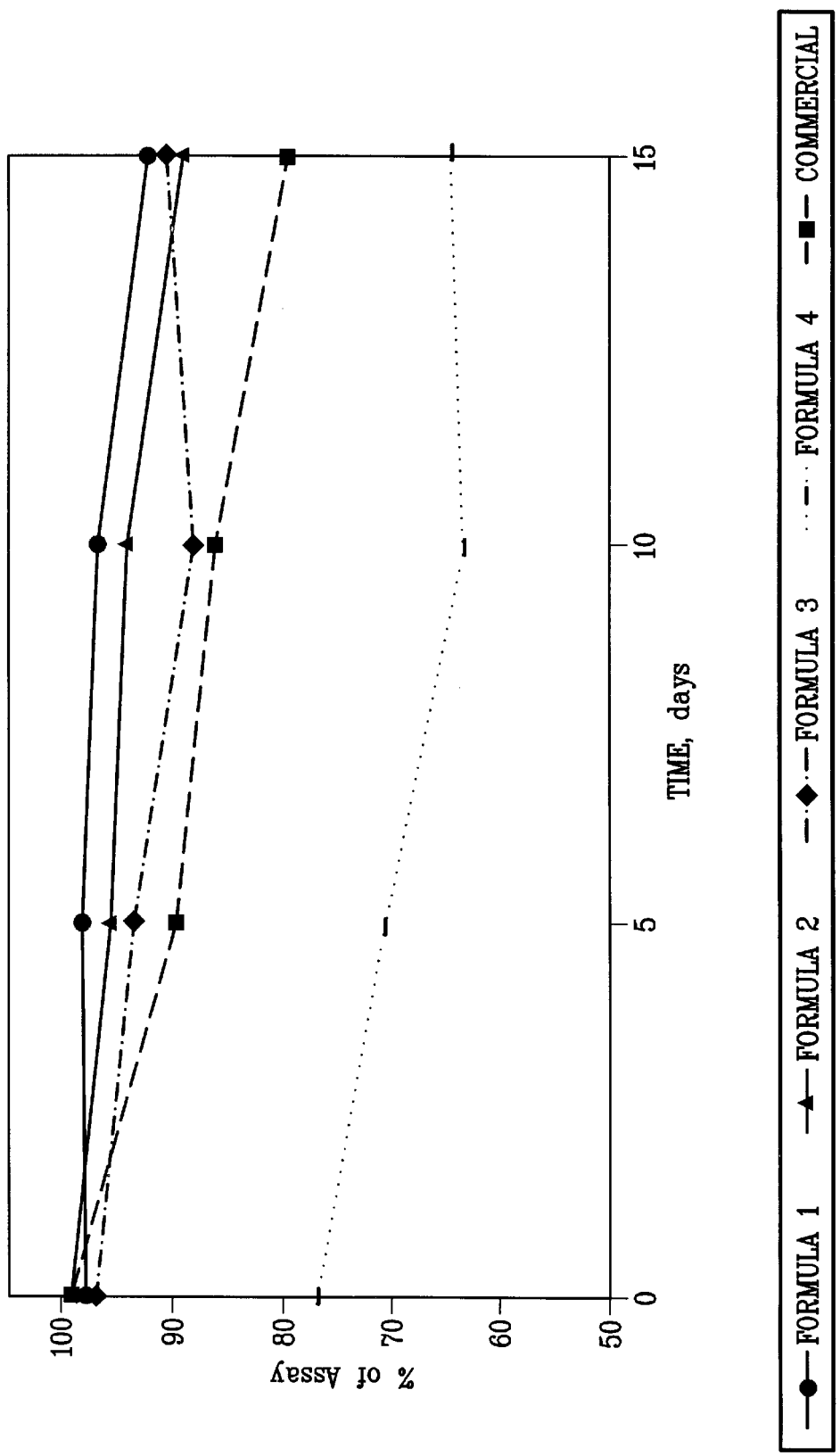
FIG. 1 depicts stability profiles of different formulations of enalapril sodium.

The practice of the present invention employs, unless otherwise indicated, conventional methods of chemistry and drug synthesis and formulation, all within the skill of the art. Such techniques are explained fully in the literature. See, e.g., Remington's Pharmaceutical Sciences, 18th Edition (Easton, Pennsylvania: Mack Publishing Company, 1990), incorporated herein by reference.

The present invention arises from the surprising discovery that it is possible to provide for the rapid, economical preparation of ACE inhibitors while minimizing breakdown of the product and maximizing the final purity of that product. Breakdown may be due to factors including, but not limited to, hydrolysis and cyclization. Cyclization may be due to factors including, but not limited to, internal nucleophilic attack. Formulations of stabilized ACE inhibitors, especially those of enalapril sodium, are also provided. Although not wishing to be bound by theory, the inventor believes that the presence of alcohol, as described hereinafter, not only accelerates the manufacture of the product but also minimizes extensive hydrolysis and/or cyclization of the product during production and storage. Surprisingly, it has also been found that the presence of cellulosic materials in the present method results in formulations that are substantially free of breakdown products; in the case of enalapril maleate, resulting in formulations which are substantially free of enalaprilat and/or enalapril-DKP.

As used herein, the phrase "stabilized ACE inhibitor" refers to ACE inhibitors prepared according to the present invention, and is meant to encompass an ACE inhibitor salt with a metal compound. As used herein, the term "DKP" or "diketopiperazine" includes DKP-compounds of the ACE inhibitor. For example, the DKP breakdown product of enalapril maleate, enalapril-DKP, is encompassed by the term "DKP" or "diketopiperazine".

The term "substantially free" refers to compositions that have significantly reduced levels of detectable breakdown products, e.g. enalaprilat and/or enalapril-DKP in the case of enalapril maleate. In one embodiment, the enalapril sodium contains less than about 5% enaliprilat, preferably less than 2.5% enaliprilat, or, even more preferably, less than about 1%, or, in the case of other ACE inhibitors, a similarly small quantity of analogous impurity. In another embodiment, the enalapril sodium contains less than about 1.0% DKP, more preferably less than about 0.5% DKP, or, even more preferably, less than about 0.25% DKP or, in the case of other ACE inhibitors, a similarly small quantity of analogous impurity. In another embodiment, the enalapril sodium contains less than about 5% enaliprilat and less than about 1% DKP, or, in the case of other ACE inhibitors, a similarly small quantity of analogous impurities.

As used herein, the term "analogous breakdown product", "degradation product", or "analogous impurity" or derivatives thereof, refer to undesired contaminants formed by breakdown of an ACE inhibitor which are similar, as appreciated by persons of ordinary skill in the art, to those resulting from enalapril breakdown. Breakdown of ACE inhibitors may be caused by factors including, but not limited to, hydrolysis and cyclization.

The present invention provides methods of preparing stable formulations of ACE inhibitors, especially enalapril sodium. The methods comprise the steps of mixing an ACE inhibitor, for example enalapril maleate, with an alcohol to form an alcoholic dispersion, dissolving or dispersing a metal compound in water to form a metal compound solution or dispersion, and mixing together the alcoholic dispersion of the ACE inhibitor and the aqueous solution or dispersion of the metal compound. In some embodiments, the mixture of the alcoholic dispersion is mixed with the aqueous solution or dispersion of the metal compound until a clear solution is attained. In other embodiments the method further comprises adding at least one excipient to the clear solution. Alternative embodiments further comprise adding an antioxidant to the alcoholic dispersion. Some embodiments further comprise blending at least one excipient and the clear solution to form a granulate. In other embodiments, the granulates are dried and preferably processed into a pharmaceutical solid, e.g. tablet, particulate and the like.

As used herein, the term "alcohol" refers to lower, e.g. $C_1$ to $C_6$, monohydric alcohols acceptable for pharmaceutical preparations, especially ethanol. While polyhydric alcohols may be used, they are generally more toxic and are not preferred. The terms "alcohol" and "alcoholic" include water/alcohol mixtures—hydroalcoholic systems.

As used herein, the term "metal compound" refers to a compound added to the ACE inhibitor to effect its conversion to the stabilized ACE inhibitor. Metal compounds useful in connection with this invention are basic salts of alkali and alkaline earth metals which are readily water soluble and which do not interfere with the stability of the compositions of the present invention. Thus, the readily water and/or alcohol-soluble salts of lithium, sodium, potassium, cesium, rubidium, calcium, magnesium, strontium and barium, bicarbonate, carbonate, hydroxide, acetate, borate and similar materials may be employed herein as the metal compound. Preferred among these are sodium, potassium, calcium, and magnesium salts, especially sodium salts. Counterions which are preferred are bicarbonate, hydroxide and carbonate, with bicarbonate being most preferred. Sodium bicarbonate is most preferred for certain embodiments of the invention. This includes, but is not limited to, sodium bicarbonate, sodium hydroxide, sodium acetate, and sodium borate. While sodium is the conventional and preferred ion, potassium and other pharmaceutically acceptable anions may be employed and all such will be understood to be encompassed hereby.

As used herein, the term "antioxidant" refers to a composition which reduces or prevents oxidation. "Antioxidants" include, but are not limited to, butyl hydroxyl anisol (BHA), butyl hydroxyl toluene (BHT), maleic acid, and ascorbic acid. In a preferred embodiment the antioxidant is maleic acid, and is present in an amount from about 0.001% to about 2.0% w/w per unit dose.

In one embodiment of the present invention, the method further comprises the addition of a thickening agent to the metal compound solution or dispersion. As used herein, the term "thickening agent" is well known to those of skill in the art. A wide variety of thickening agents may be used to a prepare the stable formulations of the present invention. Suitable thickening agents include any and all biocompatible agents known to function as thickening agents. In a preferred embodiment of the present invention, the thickening agent is selected from the group consisting of polyethylene glycol, propylene glycol, glycerin, and polyvinylpyrrolidone. In a more preferred embodiment, the thickening agent is polyvinylpyrrolidone, and is present in an amount from about 1% to about 5% w/w per unit dose.

Tabletting and other pharmaceutically acceptable excipients may be blended with the dry material provided hereby to facilitate formation of conventional and convenient pharmaceutical solids. Such formulation is known per se.

As used herein, the term "clear solution" refers to the solution attained after complete or substantially complete conversion of ACE inhibitor to the stabilized ACE inhibitor. The term "clear solution" may refer to a substantially clear material having some coloration, typically a yellowish tint, which may appear to be colloidal. This definition includes solutions which are partly cloudy. For example, as used for the end-point for complete conversion of enalapril maleate to enalapril sodium, the term "clear solution" refers to the relative absence of foamation or bubbling. The presence of a "clear solution" is measured by eye, assessing the absence of foamation.

The term "excipient" includes, but is not limited to, the family of modified celluloses such as carboxymethyl and ethyl cellulose, hydroxyethyl cellulose, microcrystalline cellulose and others. In one embodiment, the excipient is at least one of microcrystalline cellulose, starch, and sodium starch glycolate.

In one embodiment of the present invention, a pharmaceutical preparation comprising a pharmaceutically acceptable salt of a stabilized ACE inhibitor substantially free of breakdown products is provided. In a preferred embodiment, the ACE inhibitor is enalapril maleate, the stabilized ACE inhibitor is enalapril sodium, and the breakdown products are enalaprilat and/or enalapril-DKP.

In still another embodiment of the present invention, pharmaceutical preparations are provided comprising a pharmaceutically acceptable salt of a stabilized ACE inhibitor and microcrystalline cellulose, substantially free of breakdown products. In a preferred embodiment, the ACE inhibitor is enalapril maleate, the stabilized ACE inhibitor is enalapril sodium, and the breakdown products are enalaprilat and/or enalapril-DKP.

Microcrystalline cellulose is known per se and a variety of such are commercially available. Exemplary among these is the family of products sold by the FMC Corporation under the trademark Avicel®. Any of the members of this family may be used in connection with the practice of one or more embodiments of the present invention and all are contemplated hereby. Other cellulose products which are similar in nature to microcrystalline cellulose may find utility herein, such a parenchymal cell cellulose.

In addition to the preferred microcrystalline celluloses and similar materials, other cellulosic materials may also be employed in connection with one or more embodiments of the present invention. Thus, modified celluloses such as methyl cellulose, hydroxyethyl cellulose, hydroxypropyl cellulose, methylhydroxyethyl cellulose, methylhydroxypropyl cellulose, carboxymethyl cellulose salts and esters, (e.g. sodium, potassium etc. salts), and other cellulose derivatives may be so employed. It will be appreciated by persons of ordinary skill in the art that such cellulosic materials should be consistent with the overall spirit of the invention. Thus, such materials may be employed which do not adversely effect the processing set forth herein and which do not interfere with the stability of the to resulting products.

Those of skill in the art will also understand that the term "excipient" is used colloquially to include such agents as disintegrating agents, carriers, diluents, pigments, binders, colorants, and lubricants. In one embodiment, the excipient is a disintegrating agent.

The term "disintegrating agent" is well known to those of skill in the art as an agent that enhances the conversion of a compact material into fine primary particles during dissolution. Disintegrating agents include, but are not limited to, starch, cellulose, sodium starch glycolate, and modified cellulose, and are present in amounts from about 1% to about 25% w/w per unit dose.

The term "lubricant" is well known to those of skill in the art as an additive to prevent the sticking of the formulation to tooling during the tabletting process. Lubricants include, but are not limited to, stearates, hydrogenated vegetable oils, and talc. In some embodiments of the present invention, the lubricant is a stearate. In some preferred embodiments, the lubricant is magnesium stearate or glyceryl monostearate and is present in an amount from about 0.5% to about 10% w/w per unit dose. In a more preferred embodiment, the lubricant is magnesium stearate and is present in an amount from about 0.01% to about 1% w/w per unit dose.

The term "binder" is well known to those of skill in the art as an agent that holds the components of the formulation together. Binders include, but are not limited to, gelatin, polyvinylpyrrolidone (PVP), hydroxypropyl methylcellulose (HPMC), starch grades (pregelatinized or plain), hydroxypropylcellulose (HPC), and carboxymethylcellulose (CMC), and their salts.

As used herein, the term "drying" refers to the substantial removal of liquid from the granulation. Drying may be accomplished in a number of manners well known to those of skill in the art including, but not limited to the use of ovens, fluid bed driers, and other similar equipment. In a preferred embodiment, the granulation is dried for about 12 hours at 50° C. to substantially remove liquid from the granulation.

As used herein, the term "pharmaceutical solid dosage forms" refers to the final solid pharmaceutical product. The term "pharmaceutical solid dosage form" includes, but is not limited to, tablets, caplets, beads, and capsules (including both hard shell capsules and soft gelatin capsules).

The processes of mixing, drying, granulating and making pharmaceutical solid formulations are well known to those of skill in the art. See, e.g., Theory & Practice of Industrial Pharmacy, $3^{rd}$ Edition, Liberman, Lachman, and Kanig, eds. (Philadelphia, Pennsylvania: Lea & Febiger), incorporated herein by reference.

By "pharmaceutically acceptable" or "pharmacologically acceptable" is meant a material which is not biologically or otherwise undesirable, i.e., the material can be administered to an individual along with the stabilized ACE inhibitor formulation without causing any undesirable biological effects or interacting in a deleterious manner with any of the components of the formulation in which it is contained.

EXAMPLES

Below are several examples of specific embodiments for carrying out the present invention. The examples are offered for illustrative purposes only, and are not intended to limit the scope of the present invention in any way.

Example 1

Materials and Methods
Synthesis of Formula I

Enalapril maleate (20 grams; Byron Chem. Co., Long Island City, N.Y.) were suspended in denatured alcohol (50 grams, SD3A) with stirring at 500 rpm. Full dispersion of the enalapril maleate in the alcohol was achieved in less than about 10 seconds. In a separate container, sodium bicarbonate (11 grams) and povidone (poly(1-vinyl-2-pyrrolidinone) homopolymer) (9 grams, PVP K29/32) were dissolved in 100 mL purified water (USP). The sodium bicarbonate/povidone solution was added gradually to the alcoholic drug dispersion with constant stirring (200 rpm) until a clear solution was achieved to yield solution 1, e.g. the solution was free of foaming (bubbling).

Microcrystalline cellulose (225 grams, Avicel PH200; FMC Corporation, Philadelphia, Pa.), sodium starch glycolate (30 grams, Explotab; Edward Mendell Co., New York, N.Y.), and silicon dioxide (8 grams; Syloid 244 FP; W. R. Grace & Co., Baltimore, Md.) were mixed for three minutes in a high shear mixer for 3 minutes (Collete Gral 10) to yield mixture 1. Mixture 1 was blended with solution 1 for three minutes at low speed with the choppers set to low. The resulting granulation was then dried for 12 hours at 50° C. The dried granulation was then passed through a #30 mesh screen and blended with magnesium stearate (2 grams), producing the final tabletting blend of Formula I.

Synthesis of Formula II

Formula II was synthesized according to the methods set forth for Formula I with the following variation. Enalapril maleate was suspended in denatured alcohol (30 grams, SD3A) and Tween80 (20 grams; Sigma, St. Louis, Mo.) with stirring at 500 rpm.

Synthesis of Formula III

Enalapril maleate (20 grams; Byron Chem. Co., Long Island City, N.Y.) were suspended in purified water (50 grams, USP) with stirring at 500 rpm. In a separate container, sodium bicarbonate (11 grams) and povidone (9 grams; PVP K29/32) were dissolved in purified water (100 grams, USP). The sodium bicarbonate/povidone solution was added gradually to the drug dispersion with constant stirring (200 rpm) until an almost clear solution was achieved to yield solution 2.

Microcrystalline cellulose (225 grams; Avicel PH200; FMC, Philadelphia, Pa.), sodium starch glycolate (30 grams, Explotab; Edward Mendell Co., New York, N.Y.), and silicon dioxide (8 grams, Syloid 244 FP; W. R. Grace & Co., Baltimore, Md.) were mixed for three minutes in a high shear mixer for 3 minutes (Collete Gral 10) to yield mixture 2. Mixture 2 was blended with solution 2 for three minutes at low speed with the choppers set to low. The resulting granulation was then dried for 12 hours at 50° C. The dried granulation was then passed through a #30 mesh screen and blended with magnesium stearate (2 grams), producing the final tabletting blend of Formula III.

Synthesis of Formula IV

Formula IV was synthesized according to the methods set forth for Formula III with the following variation. Enalapril maleate was suspended in purified water (30 mg/ud, USP) and Tween® 80 (20 mg/ud; Sigma, St. Louis, Mo.) with stirring at 500 rpm.

Formulations I and II were made according to the present invention, while Formulations III and IV were made according to Merslavic et al. in terms of conversion of enalapril maleate to enalapril sodium. However, unlike the methods described in Merslavic et al., Formulations III and IV were prepared using microcrystalline cellulose instead of starch and cellulose as the diluent.

Example 2

Comparison of Stability Profiles of Different Formulations of Enalapril Sodium.

The stability profiles of different formulations of enalapril maleate were compared. The stability of formulations of enalapril sodium (Formulas I–IV, as described above) were also compared to a commercial formulation of enalapril maleate, VASOTEC™ (Merck & Co.) referred to as "commercial." Formulations were stored at 60° C. with 75% relative humidity to simulate extended storage. Stability of the formulations was assessed at 5, 10, and 15 days by HPLC.

As shown in FIG. 1, Formulation I was more stable than the VASOTEC™ formulation and Formulations II–IV at the 5, 10, and 15 day timepoints. At the 5 and 10 day timepoints, Formulation II exhibited greater stability than Formulations III, IV, and the VASOTEC™ formulation, referred to as the "commercial formulation." Formulation II was more stable at the 5, 10, and 15 day timepoints than the VASOTEC™ formulation and Formulation IV.

Example 3

The levels of impurities in different formulations of enalapril maleate were compared. The level of impurities of the formulations of enalapril maleate were also compared to a commercial formulation of enalapril maleate, VASOTEC™. Formulations were stored at 60° C. with 75% relative humidity to simulate extended storage. Impurity levels of the formulations were assessed at 5, 10, and 15 days by measurement of enalaprilat and enalapril-DKP formation by HPLC.

As shown in FIG. 2, at the 10 and 15 day timepoints, Formulation I exhibited the greatest purity; e.g. the lowest level of impurity. At the 10 and 15 day timepoints, Formulation I had less impurities than did Formulations III, IV, and VASOTEC™.

Formulation II exhibited less impurities than did Formulations III, IV, and VASOTEC™ at the 10 and 15 day timepoints.

Example 4

Effect of Alcohol/Water Ratio on Dispersion Time of Enalapril Maleate.

Enalapril maleate (50 grams) were added to 200 mL of liquid. The liquid ranged from 100% alcohol/ 0% water to 0% alcohol/100% water (USP) (see Table 1). The solutions were stirred at 200 rpm at room temperature in a Lightnin® Mixer (General Signal Controls, Rochester, N.Y.) with the mixing blade 1 cm from the bottom of the beaker. Enalapril maleate was considered "dispersed" when all of the drug powder was wetted and had become immersed in the liquid.

As shown in Table 1, solutions containing high relative levels of alcohol yielded faster dispersion of enalapril maleate than did solutions containing lower relative levels of alcohol. Surprisingly, an enalapril maleate solution containing 100% alcohol had a dispersion time of 27 seconds whereas an enalapril maleate solution containing 100% water had a dispersion time of over 76 minutes.

TABLE 1

Dispersion time of enalapril maleate increased as the proportion of water in the liquid solution increased.

| % Alcohol/% Water | Volume Alcohol/Volume Water | Dispersion Time |
| --- | --- | --- |
| 100%/0% | 200 mL/0 mL | 27 seconds |
| 85%/15% | 170 mL/30 mL | 28 seconds |
| 75%/25% | 150 mL/50 mL | 30 seconds |
| 50%/50% | 100 mL/100 mL | 45 seconds |
| 25%/75% | 50 mL/150 mL | 1 minute, 15 seconds |
| 0%/100% | 0 mL/200 mL | 76 minutes, 43 seconds |

The present invention has been exemplified with respect to the pharmaceutical enalapril maleate. Persons of ordinary skill in the art will appreciate, however, that certain other drugs known to be ACE inhibitors may also suffer from the same shortcomings as enalapril maleate. The members of this class of ACE inhibitors may also benefit from employment of the present invention, and all such drugs are contemplated hereby. Among this class are the drugs quinapril, lisinopril, benazepril, indolapril and moexipril, known per se.

All publications, patents and patent applications cited herein are hereby incorporated by reference in their entirety. As used in this specification and the appended claims, the singular forms "a," "an" and "the" include plural references unless the content clearly dictates otherwise. Thus, for example, reference to "an excipient" includes a mixture of two or more excipients.

What is claimed is:

1. A method of preparing a stable formulation of enalapril maleate which comprises the steps of:

mixing enalapril maleate with an alcohol to form an alcoholic dispersion;

dispersing or dissolving a metal compound in water to form a metal compound dispersion or solution;

mixing the alcoholic dispersion and the metal compound dispersion until a clear solution is attained;

the stable formulation being substantially free of breakdown products after incubation at 60° C. with 75% relative humidity for 10 days.

2. The method of claim 1 wherein the metal compound is of an alkali metal.

3. The method of claim 1 wherein the metal compound is of an alkaline earth metal.

4. The method of claim 1 further comprising adding at least one excipient to the clear solution.

5. The method of claim 1 further comprising adding an antioxidant to said alcoholic dispersion.

6. The method of claim 5 wherein the antioxidant is selected from the group consisting of butyl hydroxyl anisol, butyl hydroxyl toluene, maleic acid, and ascorbic acid.

7. The method of claim 1 further comprising adding microcrystalline cellulose to the clear solution.

8. The method of claim 4 further comprising blending the excipient and the clear solution to form a granulate.

9. The method of claim 8 further comprising drying the granulate.

10. The method of claim 9 further comprising adding a lubricant to the dried granulate.

11. The method of claim 10 wherein the lubricant is a stearate.

12. The method of claim 11 wherein the stearate is magnesium stearate or glyceryl monostearate.

13. A method of preparing a stable formulation of enalapril maleate which comprises:

forming an alcoholic dispersion of the enalapril maleate with alcohol;

dispersing or dissolving a metal compound in water to form a dispersion or solution of the metal compound;

mixing the alcoholic dispersion and the metal compound dispersion to form a clear solution;

the stable formulation being substantially free of enalaprilat and enalapril-DKP after incubation at 60° C. with 75% relative humidity for 10 days.

14. A stabilized formulation of enalapril maleate prepared in accordance with claim 1.

15. The stabilized formulation of enalapril maleate of claim 14 wherein the breakdown products comprise enalaprilat and enalapril-DKP.

16. The stabilized formulation of claim 14 which contains less than 5% breakdown products by weight of the enalapril maleate formulation after incubation at 60° C. with 75% relative humidity for 10 days.

17. The stabilized formulation of claim 16 which contains less than 2.5% breakdown products by weight of the enalapril maleate formulation after incubation at 60° C. with 75% relative humidity for 10 days.

18. The stabilized formulation of claim 17 which contains less than 1% breakdown products by weight of the enalapril maleate formulation after incubation at 60° C. with 75% relative humidity for 10 days.

19. A stabilized formulation of enalapril maleate prepared in accordance with claim 13.

20. The stabilized formulation of claim 19 which contains less than 5% enalaprilat and enalapril-DKP by weight of the enalapril maleate formulation after incubation at 60° C. with 75% relative humidity for 10 days.

21. The stabilized formulation of claim 20 which contains less than 2.5% enalaprilat and enalapril-DKP by weight of the enalapril maleate formulation after incubation at 60° C. with 75% relative humidity for 10 days.

22. The stabilized formulation of claim 21 which contains less than 1% enalaprilat and enalapril-DKP by weight of the enalapril maleate formulation after incubation at 60° C. with 75% relative humidity for 10 days.

* * * * *